United States Patent
Ogunwobi et al.

(10) Patent No.: US 10,138,481 B2
(45) Date of Patent: Nov. 27, 2018

(54) MIRNAS USEFUL FOR IDENTIFYING TARGETS ASSOCIATED WITH CANCER

(71) Applicant: Research Foundation of the City University of New York, New York, NY (US)

(72) Inventors: Olorunseun O. Ogunwobi, Yonkers, NY (US); Dibash K. Das, Brooklyn, NY (US)

(73) Assignee: Research Foundation of the City University of New York, New York, NY (US)

( * ) Notice: Subject to any disclaimer, the term of this patent is extended or adjusted under 35 U.S.C. 154(b) by 0 days.

(21) Appl. No.: 15/338,704

(22) Filed: Oct. 31, 2016

(65) Prior Publication Data

US 2017/0121711 A1 May 4, 2017

Related U.S. Application Data

(60) Provisional application No. 62/247,788, filed on Oct. 29, 2015, provisional application No. 62/301,692, filed on Mar. 1, 2016, provisional application No. 62/350,277, filed on Jun. 15, 2016.

(51) Int. Cl.
    *C12N 15/113* (2010.01)
    *C12Q 1/6886* (2018.01)

(52) U.S. Cl.
    CPC .......... *C12N 15/113* (2013.01); *C12Q 1/6886* (2013.01); *C12N 2310/141* (2013.01); *C12N 2310/53* (2013.01); *C12Q 2600/178* (2013.01)

(58) Field of Classification Search
    None
    See application file for complete search history.

(56) References Cited

U.S. PATENT DOCUMENTS 5,972,602 A    10/1999  Hyland et al.

OTHER PUBLICATIONS

Das et al (Cancer Research 76(14, Supplement) Abstract 1074, Jul. 2016) (Year: 2016).*
Dermer (Biotechnology 12: 320, 1994) (Year: 1994).*
Gillet (Proc. Nat. Acad. Sci. USA 108(46):18708-18713, 2011) (Year: 2011).*
Wani, S. et al.; Profiling direct mRNA-microRNA interactions using synthetic biotinylated microRNA-duplexes; Detailed Laboratory Protocol; May 19, 2014; pp. 1-11; QIMR Berghofer MRI l.
Ørom, U. et al.; MicroRNA-10a Binds the 50UTR of Ribosomal Protein mRNAs and Enhances Their Translation; Molecular Cell; May 23, 2008; pp. 460-471; vol. 30; Elsevier Inc.
Ørom, U. et al.; Isolation of microRNA targets using biotinylated synthetic microRNAs; Methods; Oct. 2007; pp. 162-165; vol. 43; Elsevier Inc.
Das, D. et al; miR-1207-3p regulates the androgen receptor in prostate cancer via FNDC1/fibronectin; Experimental CellResearch; Sep. 29, 2016; pp. 190-200; vol. 348; Elsevier Inc.
Das, D. et al; miR-1207-3p Is a Novel Prognostic Biomarker of Prostate Cancer1; Translational Oncology; Jun. 2016; pp. 236-241; vol. 9 No. 3.
Cloonan, Nicole; Re-thinking miRNA-mRNA interactions: Intertwining issues confound target discovery; Bioessays; Feb. 12, 2015; pp. 379-388; vol. 37; Wiley Periodicals, Inc.
Guo, Y. et al.; 3'-Biotin-tagged microRNA-27 does not associate with Argonaute proteins in cells; May 12, 2014; RNA; pp. 9885-988; vol. 20, No. 7; Cold Spring Harbor Laboratory Press for the RNA Society.
Exiqon; microRNA target identification by RNA pull down with biotinylated microRNA mimics; Exiqon; Dec. 2014.

* cited by examiner

*Primary Examiner* — Richard A Schnizer
(74) *Attorney, Agent, or Firm* — Peter J. Mikesell; Schmeiser, Olsen & Watts, LLP

(57) ABSTRACT

Several miRNAs are described that are useful in diagnosing and treating prostate cancer, or pancreatic cancer. The miRNAs bind with targets that are associated with prostate cancer or pancreatic cancer. This permits the identification of those targets as well as a treatment methodology for prostate cancer.

10 Claims, 2 Drawing Sheets

Specification includes a Sequence Listing.

FIG. 1

| | | Position | | | | | | | | | | | | | | | | | | | | | | | | | |
|---|---|---|---|---|---|---|---|---|---|---|---|---|---|---|---|---|---|---|---|---|---|---|---|---|---|---|---|
| | | 1 | 2 | 3 | 4 | 5 | 6 | 7 | 8 | 9 | 10 | 11 | 12 | 13 | 14 | 15 | 16 | 17 | 18 | 19 | 20 | 21 | 22 | 23 | 24 | 25 | 26 |
| miR-1207-3p | | | | | | | | | | | | | | | | | | | | | | | | | | | |
| SEQ ID NO: 1 | 5' | — | — | U | C | A | G | C | U | G | G | C | C | C | A | U | U | U | C | $X_1$ | $X_2$ | | | | | | 3' |
| SEQ ID NO: 2 | 3' | $X_1$ | $X_2$ | A | U | C | G | A | C | C | G | G | G | A | U | A | A | A | G | | | | | | | | 5' |
| mir-198 | | | | | | | | | | | | | | | | | | | | | | | | | | | |
| SEQ ID NO: 3 | 5' | — | — | G | G | U | C | C | A | G | A | G | G | G | G | A | G | A | U | A | G | U | U | C | $X_1$ | $X_2$ | 3' |
| SEQ ID NO: 4 | 3' | $X_1$ | $X_2$ | C | U | A | G | G | U | C | U | C | C | C | C | U | A | U | C | A | A | G | | | | | 5' |
| mir-24-3p | | | | | | | | | | | | | | | | | | | | | | | | | | | |
| SEQ ID NO: 5 | 5' | — | — | U | G | G | C | U | C | A | G | U | U | C | A | G | C | A | G | G | A | A | C | A | G | $X_1$ | $X_2$ | 3' |
| SEQ ID NO: 6 | 3' | $X_1$ | $X_2$ | A | U | C | G | A | G | U | C | A | A | G | U | C | G | U | C | C | U | G | U | C | | | 5' |
| mir-1205 | | | | | | | | | | | | | | | | | | | | | | | | | | | |
| SEQ ID NO: 7 | 5' | — | — | U | C | U | G | C | A | G | G | G | U | U | U | G | C | U | U | U | G | A | G | $X_1$ | $X_2$ | | 3' |
| SEQ ID NO: 8 | 3' | $X_1$ | $X_2$ | A | A | A | C | G | U | C | C | C | A | A | A | C | G | A | G | A | C | U | C | | | | 5' |
| mir-1304-5p | | | | | | | | | | | | | | | | | | | | | | | | | | | |
| SEQ ID NO: 9 | 5' | — | — | U | U | U | G | A | G | G | C | U | A | C | A | G | U | G | A | G | A | U | G | U | G | $X_1$ | $X_2$ | 3' |
| SEQ ID NO: 10 | 3' | $X_1$ | $X_2$ | A | G | A | C | U | C | C | G | A | U | G | U | C | A | C | U | C | U | A | C | A | C | | 5' |

FIG. 2

Position

| | 1 | 2 | 3 | 4 | 5 | 6 | 7 | 8 | 9 | 10 | 11 | 12 | 13 | 14 | 15 | 16 | 17 | 18 | 19 | 20 | 21 | 22 | 23 | 24 | 25 | 26 |
|---|---|---|---|---|---|---|---|---|---|---|---|---|---|---|---|---|---|---|---|---|---|---|---|---|---|---|
| Mutant miR-1207-3p | | | | | | | | | | | | | | | | | | | | | | | | | | |
| SEQ ID NO: 13 5' | — | — | U | C | G | C | A | U | G | G | C | C | C | U | C | A | U | U | U | C | X₁ | X₂ | | | | |
| SEQ ID NO: 14 3' | X₁ | X₂ | A | U | C | G | U | A | C | C | G | G | G | A | C̲ | U | A | A | A | G | | | | | | |
| Mutant miR-198 | | | | | | | | | | | | | | | | | | | | | | | | | | |
| SEQ ID NO: 15 5' | — | — | G | G | G | U | A | A | G | A | G | C | C | A | G | A | U | A | G | U | U | C | X₁ | X₂ | | |
| SEQ ID NO: 16 3' | X₁ | X₂ | C | U̲ | C | A | U | U | C | U | C | A | C | U | C | C | U | A | A | G | | | | | | |
| Mutant miR-24-3p | | | | | | | | | | | | | | | | | | | | | | | | | | |
| SEQ ID NO: 17 5' | — | — | U | G | U | A | G | C | A | G | U | U | C | A | G | C | A | G | G | A | A | C | A | G | X₁ | X₂ |
| SEQ ID NO: 18 3' | X₁ | X₂ | A | U̲ | C | G | U | C | A | A | G | U | C | G | U | C | C | U | U | G̲ | U | C | | | | |
| Mutant miR-1205 | | | | | | | | | | | | | | | | | | | | | | | | | | |
| SEQ ID NO: 19 5' | — | — | U | C | C | U | G | A | G | G | G | U | U | U | C | A | G | C | U | U | U | G | A | G | X₁ | X₂ |
| SEQ ID NO: 20 3' | X₁ | X₂ | A | A | G | A | C | U | C | C | C | A | A | A | C | G | A | G̲ | A | C | U | C | | | | |
| Mutant miR-1304-5p | | | | | | | | | | | | | | | | | | | | | | | | | | |
| SEQ ID NO: 21 5' | — | — | U | U | A | G | U | G | G | C | U | A | C | A | G | U | A | C | A | G | A | U | G | X₁ | X₂ | |
| SEQ ID NO: 22 3' | X₁ | X₂ | A | G̲ | U | C | A | C | C | G | A | U | C | A | C | A | U | C | U | G | U | A | C | | | |

MIRNAS USEFUL FOR IDENTIFYING TARGETS ASSOCIATED WITH CANCER

CROSS-REFERENCE TO RELATED APPLICATIONS

This application claims priority to, and is a non-provisional of, U.S. provisional patent applications 62/247,788 (filed Oct. 29, 2015); 62/301,692 (filed Mar. 1, 2016) and 62/350,277 (filed Jun. 15, 2016) the entirety of which are incorporated herein by reference.

STATEMENT OF FEDERALLY SPONSORED RESEARCH OR DEVELOPMENT

This invention was made with government support under grant number MD007599 awarded by the National Institute of Minority Health and Health Disparaties, National Institute of Health (NIMHD/NIH). The government has certain rights in the invention.

REFERENCE TO A SEQUENCE LISTING

This application refers to a "Sequence Listing" listed below, which is provided as an electronic document entitled "Sequence.txt" (10 kb created on Oct. 24, 2016) which is incorporated herein by reference in its entirety.

BACKGROUND OF THE INVENTION

MicroRNAs (miRNAs) are regulators of gene expression that often suppress the translation of protein coding mRNAs through a RNA-induced silencing complex (RISC). Although some methods of identifying miRNA targets are available (e.g. luciferase assays) these methods are laborious, expensive and imperfect.

Methods of identifying miRNA targets is described in articles entitled "MicroRNA-10a Binds the 5'UTR of Ribosomal Protein mRNAs and Enhances Their Translation" by Orom et al. (Mol. Cell 30, 460-71, 2008) and "Isolation of microRNA targets using biotinylated synthetic microRNAs" by Orom et al. (Methods 43, 162-5, 2007). Also see an article entitled "Profiling Direct mRNA-microRNA interactions using synthetic biotinylated microRNA-duplexes" by Wani et al. (printed online at BioRxIV, May 22, 2014). These techniques are referred to as RNA pull-down assays. Briefly, a miRNA of interest in synthesized with a 3'biotin group. The miRNA binds to its mRNA targets in cells. The resulting complex is separated from other cellular materials by, for example, streptavidin beads, purified and subjected to PCR, microarray or sequencing analysis to identify the molecular targets of the miRNA.

The discussion above is merely provided for general background information and is not intended to be used as an aid in determining the scope of the claimed subject matter.

BRIEF DESCRIPTION OF THE INVENTION

Several miRNAs are described that are useful in diagnosing and treating certain cancers. The miRNAs bind to molecular targets that are associated with specific cancers. This permits the identification of those targets as well as a treatment methodology for cancer. A method for the quantification of the miRNAs is also provided.

This brief description of the invention is intended only to provide a brief overview of subject matter disclosed herein according to one or more illustrative embodiments, and does not serve as a guide to interpreting the claims or to define or limit the scope of the invention, which is defined only by the appended claims. This brief description is provided to introduce an illustrative selection of concepts in a simplified form that are further described below in the detailed description. This brief description is not intended to identify key features or essential features of the claimed subject matter, nor is it intended to be used as an aid in determining the scope of the claimed subject matter. The claimed subject matter is not limited to implementations that solve any or all disadvantages noted in the background.

BRIEF DESCRIPTION OF THE DRAWINGS

So that the manner in which the features of the invention can be understood, a detailed description of the invention may be had by reference to certain embodiments, some of which are illustrated in the accompanying drawings. It is to be noted, however, that the drawings illustrate only certain embodiments of this invention and are therefore not to be considered limiting of its scope, for the scope of the invention encompasses other equally effective embodiments. The drawings are not necessarily to scale, emphasis generally being placed upon illustrating the features of certain embodiments of the invention. In the drawings, like numerals are used to indicate like parts throughout the various views. Thus, for further understanding of the invention, reference can be made to the following detailed description, read in connection with the drawings in which:

FIG. 1 is a depiction of certain miRNA duplexes showing their relative alignments and overhangs; and FIG. 2 is a depiction of certain mutant miRNA duplexes showing their relative alignments and overhangs.

DETAILED DESCRIPTION OF THE INVENTION

This disclosure pertains to the discovery that certain miRNAs have an altered expression in some prostate cancer (PCa) cell lines, pancreatic cancer cell lines or gastric cancer cell lines in comparison to corresponding non-tumorigenic cell lines. These miRNAs are summarized in FIG. 1 and are referred to as miR-1207-3p (SEQ ID NO: 1, under-expressed in prostate cancer cell lines); miR-198 (SEQ ID NO: 3, under-expressed in pancreatic cancer cell lines); miR-24-3p (SEQ ID NO: 5, under-expressed in gastric cancer cell lines); miR-1205 (SEQ ID NO: 7, under-expressed in prostate cancer cell lines) and miR-1304-5p (SEQ ID NO: 9, over-expressed in prostate cancer). Furthermore, in ongoing clinical studies, miR-1207-3p has been found to be a prognostic biomarker in prostate cancer. However, there is currently no commercially available biotinylated mimic for use in the discovery of corresponding molecular targets. The ability to identify molecular targets of these miRNAs is important to understanding the molecular mechanisms of action of these miRNAs.

A series of miRNA sequences are disclosed. One synthetic biotinylated miR-1207-3p duplex comprises a twenty nucleotide sequence of miR-1207-3p (UCAGCUGGCCCUCAUUUCX$_1$X$_2$, SEQ ID NO: 1) wherein X$_1$X$_2$ provide a two nucleotide overhang that forms a mature strand. In one embodiment, X$_1$X$_2$ are UG. Biotin is connected to the 3' hydroxyl group (OH) via a linker, such as a C6 linker. A passenger strand (GAAAU CAGGGCCAGCUUAX$_2$X$_1$, SEQ ID NO: 2) is provided. In one embodiment X$_2$X$_1$ are UG. For simplicity of illustration the passenger strands in the figures are depicted from 3' to 5' to shown their alignment with the corresponding mature strand. The passenger strand is complementary to the mature strand with the following exceptions: 1) there is a mismatch with position two of the mature strand, 2) other mismatches between the strands help improve disassociation of the two strands. This disassociation allows for the incorporation of the mature strand into the RNA-induced silencing complex (RISC). In one embodiment, the passenger strand has between twenty and thirty residues including a second overhang of between two and seven residues. In one embodiment, there are fewer than twenty-five residues. The passenger strand is hydrogen bonded to the mature strand and is at least 80% complementary, but less than 100% complementary with respect to the mature strand such that there is at least one mismatch. Mismatches are bolded. In one embodiment the mature strand is at least 90% complementary. In one embodiment, there is at least one mismatch between the mature strand and the passenger strand. In another embodiment there are at least two mismatches between the mature strand and the passenger strand.

Also, both strands (mature and passenger) have a 5' phosphate group and a 3' hydroxyl group. Both strands end in a two nucleotide arbitrary overhang on the 3' end.

Another synthetic biotinylated miR-198 duplex comprises a twenty-four nucleotide sequence of miR-198 (GGUCCAGAGGGGAGAUAGGUUCCUX$_1$X$_2$, SEQ ID NO: 3) wherein X$_1$X$_2$ provide a two nucleotide overhang that forms a mature strand. In one embodiment, X$_1$X$_2$ are CU. Biotin is connected to the 3' hydroxyl group (OH) via a linker, such as a C6 linker. A passenger strand (GAAC-CUAUCUC<u>A</u>CCUCUGGA<u>U</u>CX$_2$X$_1$, SEQ ID NO: 4) is provided. In one embodiment, X$_2$X$_1$ are AG.

Another synthetic biotinylated miR-24-3p twenty-four nucleotide sequence of miR-24-3p (UGGCUCAGUUCA-GCAGGAACAG~~UC~~ X$_1$X$_2$, SEQ ID NO: 5) wherein X$_1$X$_2$ provide a two nucleotide overhang that forms a mature strand. In one embodiment, X$_1$X$_2$ are UC. Biotin is connected to the 3'hydroxyl group (OH) via a linker, such as a C6 linker. A passenger strand (CUG <u>C</u>UCCUGCUGAACUGAGC<u>U</u>AX$_2$X$_1$, SEQ ID NO: 6) is provided. In one embodiment, X$_2$X$_1$ are GA.

Another synthetic biotinylated miR-1205 twenty-four nucleotide sequence of miR-1205 (UCUGCA-GGGUUUGCUUUGAG~~AC~~ X$_1$X$_2$, SED ID NO: 7) wherein X$_1$X$_2$ provide a two nucleotide overhang that forms a mature strand. In one embodiment, X$_1$X$_2$ are AC. Biotin is connected to the 3' hydroxyl group (OH) via a linker, such as a C6 linker. A passenger strand (CUCA <u>G</u>AGCAAACCCUGCA<u>A</u>AX$_2$X$_1$, SED ID NO: 8) is provided. In one embodiment, X$_2$X$_1$ are CU.

Another synthetic biotinylated miR-1304-5p twenty-four nucleotide sequence of miR-1304-5p (UUUGAGGC-UACAGUAGAUG~~CA~~ X$_1$X$_2$, SED ID NO: 9) wherein X$_1$X$_2$ provide a two nucleotide overhang that forms a mature strand. In one embodiment, X$_1$X$_2$ is CA. Biotin is connected to the 3' hydroxyl group (OH) via a linker, such as a C6 linker. A passenger strand (CAC <u>G</u>UCUCACACUGUAGCCUCA<u>G</u>AX$_2$X$_1$, SEQ IN NO: 10) is provided. In one embodiment, X$_2$X$_1$ are UG.

In one embodiment the above biotinylated microRNA-1207-3p duplex is used as a tool in RNA pull-down assays to discover all of the mRNA molecular targets of microRNA-1207-3p (miR-1207-3p). These targets can then be further studied for a much better understanding of miR-1207-3p-mRNA interactions and biology. The biotinylated scrambled oligonucleotide duplex serves as a negative control for the biotinylated miR-1207-3p duplex. There is no interaction with any known mRNAs. Nearly 20% of miRNA-mediated repression of target mRNAs occur without the canonical base pairing to the seed sequence, but rather by imperfect binding to the center of the miRNA sequence. Therefore, using this synthetic biotinylated duplex, an RNA pulldown method permits one to definitively discover any molecular targets of the mature strand. After the molecular targets are identified, there are many biological assays that can be performed to determine the functions and mechanisms of actions of the miRNA-mRNA interactions.

In addition, based on recent findings from in vitro studies of miR-1207-3p function, this synthetic biotinylated miR-1207-3p may have therapeutic applications. It may also have applications as a component tool of a highly quantitative clinical-grade diagnostic assay for prostate cancer. The disclosed synthetic biotinylated miRNA compositions also have applications as components of highly quantitative clinical-grade diagnostic assays for various diseases including cancers, and they may also have applications as bioimaging tools. Furthermore, the disclosed duplexes can be cloned into an expression plasmid, then used in establishing stable cell lines to evaluate the role of miR-1207-3p in in vivo prostate tumorigenesis. The disclosed synthetic microRNA duplexes can be used in non-viral methods of RNA delivery such as via nanoparticles to protect the miRNAs from degradation as well as increase their half-life in circulation. Thus, these microRNA duplexes via targeted delivery have the potential to produce even more pronounced therapeutic effects on cancers and other diseases.

Negative Control

The design of the negative control-scrambled oligonucleotide with biotin is made using the same approach as the miR-1207-3p biotinylated duplex with one added consideration. The mature strand, which comprises a scrambled sequence, was based on the same nucleotide composition as the miR-1207-3p sequence. The scrambled sequence (GUUCCACCGUCCUCUGUAX$_1$X$_2$, SEQ ID NO: 11) was then verified by the NCBI BLAST computer algorithm to confirm that it did not have a match for any known miRNA SEED recognition sequence. In one embodiment, X$_1$X$_2$ is UG. Furthermore, the scrambled sequence did not have any 100% match with any mRNA of the human database. The corresponding passenger strand is given by UACAGGGGACGGUGGACCX$_2$X$_1$ (SEQ ID NO: 12). In one embodiment, X$_2$X$_1$ is UG.

Mutated Sequences as Negative Controls

In some embodiments, mutated forms of one of the duplexes described above are used as a negative control. They have been verified to have no match for any known miRNA SEED recognition sequence nor do they have any 100% match with any documented human mRNA. The designs of the mutant microRNA duplexes were made using the same approach as the duplexes with the following added consideration: microRNA seed site positions 2-7 are used for direct miRNA-mRNA target recognition in all major target site types. Disrupting base pairing between miRNA positions 2-7 and the mRNA target site by mutating multiple nucleotides inhibits direct molecular mRNA targeting. Nucleotides 3 to 5 from the 5' end of the mature strand of each microRNA were arbitrarily changed. The changed sequence was based on the same nucleotide composition of the original microRNA sequence. The mutated sequences were then verified by the NCBI BLAST computer algorithm to confirm that they did not have a match for any known miRNA SEED recognition sequence. Furthermore, the mutated sequence did not have any 100% match with any mRNA of the human database.

The mutants alter three sequential nucleotides beginning at the third position in the mature strand with corresponding mutations in the passenger strand. In this fashion, SEQ ID NO: 13 (UC$\underline{X_3X_4X_5}$UGGCCCUCAUUUCX$_1$X$_2$) is a mutated form of SEQ ID NO: 1. The corresponding passenger strand is given by SEQ ID NO: 14 (GAAAUCAGGGCCA$\underline{X_5X_4X_3}$UAX$_2$X$_1$). See FIG. 2 where the passenger sequences are provided 3' to 5' to illustrate alignment with the mature strand. A summary is provided below with an example of the arbitrarily chosen mutations.

| Original SEQ. | Mutated SEQ. | Primary Structure of Mature Strand |
|---|---|---|
| SEQ ID NO: 1 | SEQ ID NO: 13 | UC$\underline{X_3X_4X_5}$UGGCCCUCAUUUCX$_1$X$_2$<br>e.g. $\overline{X_3X_4X_5}$ = GCA |
| SEQ ID NO: 2 | SEQ ID NO: 14 | GAAAUCAGGGCCA$\underline{X_5X_4X_3}$UAX$_2$X$_1$<br>e.g. $\overline{X_5X_4X_3}$ = UGC |
| SEQ ID NO: 3 | SEQ ID NO: 15 | GG$\underline{X_3X_4X_5}$AGAGGGGAGAUAGGUUCX$_1$X$_2$<br>e.g. $\overline{X_3X_4X_5}$ = GUA |
| SEQ ID NO: 4 | SEQ ID NO: 16 | GAACCUAUCUCACCUCU$\underline{X_5X_4X_3}$UCX$_2$X$_1$<br>e.g. $\overline{X_5X_4X_3}$ = UAC |
| SEQ ID NO: 5 | SEQ ID NO: 17 | UG$\underline{X_3X_4X_5}$CAGUUCAGCAGGAACAGX$_1$X$_2$<br>e.g. $\overline{X_3X_4X_5}$ = UAG |
| SEQ ID NO: 6 | SEQ ID NO: 18 | CUGCUCCUGCUGAACUG$\underline{X_5X_4X_3}$UAX$_2$X$_1$<br>e.g. $\overline{X_5X_4X_3}$ = CUA |
| SEQ ID NO: 7 | SEQ ID NO: 19 | UC$\underline{X_3X_4X_5}$AGGGUUUGCUUUGAGX$_1$X$_2$<br>e.g. $\overline{X_3X_4X_5}$ = CUG |
| SEQ ID NO: 8 | SEQ ID NO: 20 | CUCAGAGCAAACCCU$\underline{X_5X_4X_3}$AAX$_2$X$_1$<br>e.g. $\overline{X_5X_4X_3}$ = CAG |
| SEQ ID NO: 9 | SEQ ID NO: 21 | UU$\underline{X_3X_4X_5}$GGCUACAGUGAGAUGUGX$_1$X$_2$<br>e.g. $\overline{X_3X_4X_5}$ = AGU |
| SEQ ID NO: 10 | SEQ ID NO: 22 | CACGUCUCACUGUAGCC$\underline{X_5X_4X_3}$GAX$_2$X$_1$<br>e.g. $\overline{X_5X_4X_3}$ = ACU |

The design of another negative control-scrambled oligonucleotide is made using the same approach as the microRNA biotinylated duplexes with one added consideration. The mature strand, which consists of a scrambled sequence (GUUCCACCGUCCUCUGUAX$_1$X$_2$, SEQ ID NO: 23) which was verified by the NCBI BLAST computer algorithm to confirm that it did not have a match for any known miRNA SEED recognition sequence. Furthermore, the scrambled sequence did not have any 100% match with any mRNA of the human database. The corresponding passenger strand is given by UACAGGGGACGGUGGACCX$_2$X$_1$, SEQ ID NO: 24.

Non-Biotinylated MiRNAs

In one embodiment, a non-biotinylated miRNA is provided that is useful as a therapeutic. The miRNA can be administered to a patient as a treatment for prostate cancer. These non-biotinylated miRNAs are substantially identical to SEQ ID NOS. 1-10 except in that the arbitrary overhangs are omitted.

| Original SEQ. | Core SEQ. | Primary Structure |
|---|---|---|
| SEQ ID NO: 1 | SEQ ID NO: 25 | UCAGCUGGCCCUCAUUUC |
| SEQ ID NO: 2 | SEQ ID NO: 26 | GAAAUCAGGGCCAGCUUA |
| SEQ ID NO: 3 | SEQ ID NO: 27 | GGUCCAGAGGGGAGAUAGGUUC |
| SEQ ID NO: 4 | SEQ ID NO: 28 | GAACCUAUCUCACCUCUGGAUC |
| SEQ ID NO: 5 | SEQ ID NO: 29 | UGGCUCAGUUCAGCAGGAACAG |
| SEQ ID NO: 6 | SEQ ID NO: 30 | CUGCUCCUGCUGAACUGAGCUA |
| SEQ ID NO: 7 | SEQ ID NO: 31 | UCUGCAGGGUUUGCUUUGAG |
| SEQ ID NO: 8 | SEQ ID NO: 32 | CUCAGAGCAAACCCUGCAAA |
| SEQ ID NO: 9 | SEQ ID NO: 33 | UUUGAGGCUACAGUGAGAUGUG |
| SEQ ID NO: 10 | SEQ ID NO: 34 | CACGUCUCACUGUAGCCUCAGA |

Reporter System

The establishment of reporter systems for the disclosed synthetic miR-duplex will be useful tools for monitoring the tissue and cellular localization, and the molecular interactions of the synthetic duplex. These tools are desirable for the real-time monitoring of the duplex in vitro and in vivo. In one embodiment, the reporter systems comprise one of the disclosed miRNA sequences covalently coupled to Green Fluoresecent Protein (GFP) or D-Luciferin. In both of these synthetic duplex reporter systems, the recognition site (e.g. miR-1207-3p) is cloned into the 3' untranslated region (UTR) of either GFP or D-Luciferin's cDNA. The recognition site is the antisense sequence of miR-1207-3p GAAAUGAGGGCCAGCUGA (SEQ ID NO: 35). This area of the 3' UTR is known as the multicloning site (MCS) of the reporter cDNA and it is downstream of the reporter gene's open reading frame (ORF). The disclosed reporter imaging system directly incorporates the anti-sense strand specific to the miRNA nucleotide sequence for one of the disclosed miRNAs.

One application of the synthetic miRNA duplex-GFP and the miRNA duplex-D-Luciferin reporter systems is that they allow, for visual detection and monitoring of the miRNA duplex in vitro and in vivo. Moreover, these reporter systems make it possible to perform real-time monitoring and visualization of the molecular interactions of the duplex, thus enabling understanding of its functions. The method of visualizing the protein for the identification of prostate cancer introduces a miRNA composition with a structure given by one of SEQ ID NO: 1 to 11 to a biological sample. The sample may be an in vitro sample or an in vivo sample. A corresponding passenger strand is utilized that has at least one mismatch. A reporter molecule is then introduced to the biological sample. The reporter molecule comprises a visual indicator such as include green fluorescent protein and D-Luciferin.

In one embodiment, a method for absolute quantification of a miRNA using polymerase chain reaction (PCR) is provided. The method creates a standard curve using a miRNA composition with a structure given by one of SEQ ID NO: 1 to 11. A corresponding passenger strand is utilized that has at least one mismatch. An output signal is obtained from a polymerase chain reaction (PCR) that was performed on a sample such that the PCR replicates the miRNA. The output signal is compared to the standard curve to quantify the concentration of the miRNA. Method for obtaining output signals in quantitative PCR (qPCR) are known to those skilled in the art. See, for example, U.S. Pat. No. 5,972,602.

Example of Method for Finding a Molecular Target

The molecular targets of miR-1207-3p were investigated. Potential targets were initially screened using two miRNA molecular target prediction algorithm tools (miRBase and miRDB) which identified fibronectin type III domain containing 1 (FNDC1) as a putative molecular target of miR-1207-3p. FNDC1 contains the conserved 'Fibronectin type III domain' of fibronectin (FN1). FNDC1 protein expression was analyzed in several prostate epithelial cell lines (see Table 1). FNDC1 protein expression was found to be consistently higher in all the prostate cancer cell lines compared to the non-tumorigenic prostate cell line, RWPE-1. RWPE-1 had very low FNDC1 protein expression. Further, overexpression of miR-1207-3p significantly inhibited the protein expression of FNDC1 by about 75%.

TABLE 1

| Cell line | Description |
| --- | --- |
| RWPE-1 | non-tumorigenic prostate epithelial cell line from Caucasian male |
| MDA PCa 2b | aggressive, androgen-dependent, from Black male |
| PC-3 | aggressive, androgen-independent, from Caucasian male |
| E006AA | indolent, androgen-independent, from Black male |
| E006AA-hT | derived from E006AA, aggressive, androgen-independent, from Black male |
| LNCaP | aggressive, androgen-dependent, from Caucasian male |
| C4-2B | derived from LNCaP, aggressive, androgen-independent, from Caucasian male |
| WPE1-NA22 | derived from RWPE-1, indolent, androgen-dependent, from Caucasian male |

A dual-luciferase reporter assay was performed using the LUC-PAIR™ Duo-Luciferase assay system to determine if miR-1207-3p binds to the 3' untranslated region (UTR) of the FNDC1 mRNA. Prostate cancer (PCa) cell lines were used that model various characteristics of prostate cancer. Because of the significantly low level of endogenous expression of miR-1207-3p in the PC-3 and MDA PCa 2b PCa cell lines and their widespread use, these cell lines were used as cellular models for this assay. PC-3 and MDA PCa 2b cells were co-transfected with both the plasmid containing the sequence of the FNDC1 3'UTR and miR-1207-3p 50 nM mimic. Cells were transfected with 3'UTR clones of FNDC1 with a synthetic non-targeting oligonucleotide negative control as the control. A direct and specific interaction was observed between exogenous miR-1207-3p and the FNDC1 3'UTR. Overexpression of miR-1207-3p led to the suppression of activity of the luciferase reporter gene fused to the FNDC1 3'UTR by about 40% in PC-3 cells and about 60% in MDA PCa 2b cells compared to the cells transfected with the non-targeting 50 nM oligonucleotide negative control.

The miR-1207-3p was confirmed to directly bind to FNDC1 by performing RNA pulldown using our synthetic biotinylated miR-1207-3p duplex. This approach allows for the sensitive and specific detection of miRNA-mRNA interactions. MDA PCa 2b cells were transfected with either 1 nM synthetic biotinylated miR-1207-3p duplex or 1 nM synthetic biotinylated scramble duplex as control. RNA was subsequently pulled down with streptavidin coated magnetic beads. The RNA was then analyzed for FNDC1 expression with qPCR. Compared to the RNA pulled down by the synthetic biotinylated scramble duplex, the RNA pulled down by the synthetic biotinylated miR-1207-3p duplex was significantly enriched for FNDC1 by about 2000-fold. Therefore, FNDC1 is a direct molecular target of miR-1207-3p.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal language of the claims.

What is claimed is:

1. A method of treating prostate cancer, the method comprising steps of: administering a duplex micro-ribonucleic acid (miRNA) composition to a patient with prostate cancer, the duplex micro-ribonucleic acid (miRNA) composition comprising:
a mature strand comprising a primary structure of: UCAGCUGGCCCUCAUUUC (SEQ ID NO: 25); wherein the mature strand has fewer than twenty-five residues, the mature strand having a 3' end;
a passenger strand having fewer than twenty-five residues, the passenger strand being hydrogen bonded to the mature strand and at least 80% complementary, but less than 100% complementary with respect to the mature strand such that there is at least one mismatch.

2. The method as recited in claim 1, wherein the mature strand consists of UCAGCUGGCCCUCAUUUC (SEQ ID NO: 25).

3. The method as recited in claim 2, wherein the passenger strand consists of GAAAUCAGGGCCAGCUUA (SEQ ID NO: 26).

4. The method as recited in claim 1, wherein the passenger strand is at least 90% complementary, but less than 100% complementary, with respect to the mature strand.

5. The method as recited in claim 1, wherein there are at least two mismatches between the mature strand and the passenger strand.

6. A method of treating prostate cancer, the method comprising steps of:
administering a duplex micro-ribonucleic acid (miRNA) composition to a prostate cancer cell, the duplex micro-ribonucleic acid (miRNA) composition comprising:
a mature strand consisting of a primary structure of: UCAGCUGGCCCUCAUUUCX$_1$X$_2$ (SEQ ID NO: 1), wherein X$_1$ and X$_2$ are independently selected from a group consisting of A, C, G and U; and
a passenger strand consisting of a primary structure of: GAAAUCAGGGCCAGCUUAX$_2$X$_1$, (SEQ ID NO: 2), wherein X$_1$ and X$_2$ are independently selected from a group consisting of A, C, G and U, and wherein the passenger strand is hydrogen bonded to the mature strand and is less than 100% complementary with respect to the mature strand such that there are two mismatches.

7. The method as recited in claim 6, wherein X$_1$ and X$_2$ of the mature strand are U and G, respectively.

8. The method as recited in claim 7, wherein X$_1$ and X$_2$ of the passenger strand are U and G, respectively.

9. The method as recited in claim 6, wherein the prostate cancer cell is an in vitro cell line.

10. The method as recited in claim 6, wherein the prostate cancer cell is an in vivo tumor.

* * * * *

SEQUENCE LISTING

```
<160> NUMBER OF SEQ ID NOS: 35

<210> SEQ ID NO 1
<211> LENGTH: 20
<212> TYPE: RNA
<213> ORGANISM: Artificial Sequence
<220> FEATURE:
<223> OTHER INFORMATION: Synthetic mature sequence miRNA-1207-3p
<220> FEATURE:
<221> NAME/KEY: misc_feature
<222> LOCATION: (19)..(20)
<223> OTHER INFORMATION: n is a, c, g, or u

<400> SEQUENCE: 1
ucagcuggcc cucauuucnn                                                 20

<210> SEQ ID NO 2
```

```
<211> LENGTH: 20
<212> TYPE: RNA
<213> ORGANISM: Artificial Sequence
<220> FEATURE:
<223> OTHER INFORMATION: Synthetic passenger strand miRNA-1207-3p
<220> FEATURE:
<221> NAME/KEY: misc_feature
<222> LOCATION: (19)..(20)
<223> OTHER INFORMATION: n is a, c, g, or u

<400> SEQUENCE: 2
gaaaucaggg ccagcuuann                                              20

<210> SEQ ID NO 3
<211> LENGTH: 26
<212> TYPE: RNA
<213> ORGANISM: Artificial Sequence
<220> FEATURE:
<223> OTHER INFORMATION: Synthetic mature strand miR-198
<220> FEATURE:
<221> NAME/KEY: misc_feature
<222> LOCATION: (25)..(26)
<223> OTHER INFORMATION: n is a, c, g, or u

<400> SEQUENCE: 3
gguccagagg ggagauaggu uccunn                                       26

<210> SEQ ID NO 4
<211> LENGTH: 24
<212> TYPE: RNA
<213> ORGANISM: Artificial Sequence
<220> FEATURE:
<223> OTHER INFORMATION: Sythetic passenger strand miR-198
<220> FEATURE:
<221> NAME/KEY: misc_feature
<222> LOCATION: (23)..(24)
<223> OTHER INFORMATION: n is a, c, g, or u

<400> SEQUENCE: 4
gaaccuaucu caccucugga ucnn                                         24

<210> SEQ ID NO 5
<211> LENGTH: 26
<212> TYPE: RNA
<213> ORGANISM: Artificial Sequence
<220> FEATURE:
<223> OTHER INFORMATION: Synthetic mature strand of miR-24-3p
<220> FEATURE:
<221> NAME/KEY: misc_feature
<222> LOCATION: (25)..(26)
<223> OTHER INFORMATION: n is a, c, g, or u

<400> SEQUENCE: 5
uggcucaguu cagcaggaac agucnn                                       26

<210> SEQ ID NO 6
<211> LENGTH: 24
<212> TYPE: RNA
<213> ORGANISM: Artificial Sequence
<220> FEATURE:
<223> OTHER INFORMATION: Synthetic passenger strand miR-24-3p
<220> FEATURE:
<221> NAME/KEY: misc_feature
<222> LOCATION: (23)..(24)
<223> OTHER INFORMATION: n is a, c, g, or u

<400> SEQUENCE: 6
cugcuccugc ugaacugagc uann                                         24
```

```
<210> SEQ ID NO 7
<211> LENGTH: 22
<212> TYPE: RNA
<213> ORGANISM: Artificial Sequence
<220> FEATURE:
<223> OTHER INFORMATION: Synthetic mature strand miR-1205
<220> FEATURE:
<221> NAME/KEY: misc_feature
<222> LOCATION: (21)..(22)
<223> OTHER INFORMATION: n is a, c, g, or u

<400> SEQUENCE: 7
ucugcagggu uugcuuugag nn                                              22

<210> SEQ ID NO 8
<211> LENGTH: 22
<212> TYPE: RNA
<213> ORGANISM: Artificial Sequence
<220> FEATURE:
<223> OTHER INFORMATION: Synthetic passanger strand miR-1205
<220> FEATURE:
<221> NAME/KEY: misc_feature
<222> LOCATION: (21)..(22)
<223> OTHER INFORMATION: n is a, c, g, or u

<400> SEQUENCE: 8
cucagagcaa acccugcaaa nn                                              22

<210> SEQ ID NO 9
<211> LENGTH: 26
<212> TYPE: RNA
<213> ORGANISM: Artificial Sequence
<220> FEATURE:
<223> OTHER INFORMATION: Synthetic mature strand miR-1304-5p
<220> FEATURE:
<221> NAME/KEY: misc_feature
<222> LOCATION: (25)..(26)
<223> OTHER INFORMATION: n is a, c, g, or u

<400> SEQUENCE: 9
uuugaggcua cagugagaug ugcann                                          26

<210> SEQ ID NO 10
<211> LENGTH: 24
<212> TYPE: RNA
<213> ORGANISM: Artificial Sequence
<220> FEATURE:
<223> OTHER INFORMATION: Synthetic passenger strand miR-1304-5p
<220> FEATURE:
<221> NAME/KEY: misc_feature
<222> LOCATION: (23)..(24)
<223> OTHER INFORMATION: n is a, c, g, or u

<400> SEQUENCE: 10
cacgucucac uguagccuca gann                                            24

<210> SEQ ID NO 11
<211> LENGTH: 20
<212> TYPE: RNA
<213> ORGANISM: Artificial Sequence
<220> FEATURE:
<223> OTHER INFORMATION: Scrambled mature strand of miR-1207-3p
<220> FEATURE:
<221> NAME/KEY: misc_feature
<222> LOCATION: (19)..(20)
<223> OTHER INFORMATION: n is a, c, g, or u

<400> SEQUENCE: 11
guuccaccgu ccucuguann                                                 20
```

<210> SEQ ID NO 12
<211> LENGTH: 20
<212> TYPE: RNA
<213> ORGANISM: Artificial Sequence
<220> FEATURE:
<223> OTHER INFORMATION: Scrambed passenger strand of miR-1207-3p
<220> FEATURE:
<221> NAME/KEY: misc_feature
<222> LOCATION: (19)..(20)
<223> OTHER INFORMATION: n is a, c, g, or u

<400> SEQUENCE: 12
uacaggggac gguggaccnn                                              20

<210> SEQ ID NO 13
<211> LENGTH: 20
<212> TYPE: RNA
<213> ORGANISM: Artificial Sequence
<220> FEATURE:
<223> OTHER INFORMATION: Scrambled mature strand of miR-1207-3p
<220> FEATURE:
<221> NAME/KEY: misc_feature
<222> LOCATION: (19)..(20)
<223> OTHER INFORMATION: n is a, c, g, or u

<400> SEQUENCE: 13
ucbhduggcc cucauuucnn                                              20

<210> SEQ ID NO 14
<211> LENGTH: 20
<212> TYPE: RNA
<213> ORGANISM: Artificial Sequence
<220> FEATURE:
<223> OTHER INFORMATION: Scrambled passenger strand of miR-1207-3p
<220> FEATURE:
<221> NAME/KEY: misc_feature
<222> LOCATION: (19)..(20)
<223> OTHER INFORMATION: n is a, c, g, or u

<400> SEQUENCE: 14
gaaaucaggg ccahdvuann                                              20

<210> SEQ ID NO 15
<211> LENGTH: 24
<212> TYPE: RNA
<213> ORGANISM: Artificial Sequence
<220> FEATURE:
<223> OTHER INFORMATION: Scrambled mature strand of miR-198
<220> FEATURE:
<221> NAME/KEY: misc_feature
<222> LOCATION: (23)..(24)
<223> OTHER INFORMATION: n is a, c, g, or u

<400> SEQUENCE: 15
ggvddagagg ggagauaggu ucnn                                         24

<210> SEQ ID NO 16
<211> LENGTH: 24
<212> TYPE: RNA
<213> ORGANISM: Artificial Sequence
<220> FEATURE:
<223> OTHER INFORMATION: Scrambled passenger strand of miR-198
<220> FEATURE:
<221> NAME/KEY: misc_feature
<222> LOCATION: (23)..(24)
<223> OTHER INFORMATION: n is a, c, g, or u

<400> SEQUENCE: 16
gaaccuaucu caccucuhhb ucnn                                         24

```
<210> SEQ ID NO 17
<211> LENGTH: 24
<212> TYPE: RNA
<213> ORGANISM: Artificial Sequence
<220> FEATURE:
<223> OTHER INFORMATION: Scrambled mature strand of miR-24-3p
<220> FEATURE:
<221> NAME/KEY: misc_feature
<222> LOCATION: (23)..(24)
<223> OTHER INFORMATION: n is a, c, g, or u

<400> SEQUENCE: 17
ughdvcaguu cagcaggaac agnn                                              24

<210> SEQ ID NO 18
<211> LENGTH: 24
<212> TYPE: RNA
<213> ORGANISM: Artificial Sequence
<220> FEATURE:
<223> OTHER INFORMATION: Scrambled passenger strand of miR-24-3p
<220> FEATURE:
<221> NAME/KEY: misc_feature
<222> LOCATION: (23)..(24)
<223> OTHER INFORMATION: n is a, c, g, or u

<400> SEQUENCE: 18
cugcuccugc ugaacugbhd uann                                              24

<210> SEQ ID NO 19
<211> LENGTH: 22
<212> TYPE: RNA
<213> ORGANISM: Artificial Sequence
<220> FEATURE:
<223> OTHER INFORMATION: Scrambled mature strand of miR-1205
<220> FEATURE:
<221> NAME/KEY: misc_feature
<222> LOCATION: (21)..(22)
<223> OTHER INFORMATION: n is a, c, g, or u

<400> SEQUENCE: 19
ucvhdagggu uugcuuugag nn                                                22

<210> SEQ ID NO 20
<211> LENGTH: 22
<212> TYPE: RNA
<213> ORGANISM: Artificial Sequence
<220> FEATURE:
<223> OTHER INFORMATION: Scrambled passenger strand of miR-1205
<220> FEATURE:
<221> NAME/KEY: misc_feature
<222> LOCATION: (21)..(22)
<223> OTHER INFORMATION: n is a, c, g, or u

<400> SEQUENCE: 20
cucagagcaa acccuhhbaa nn                                                22

<210> SEQ ID NO 21
<211> LENGTH: 24
<212> TYPE: RNA
<213> ORGANISM: Artificial Sequence
<220> FEATURE:
<223> OTHER INFORMATION: Scrambled mature strand of miR-1304-5p
<220> FEATURE:
<221> NAME/KEY: misc_feature
<222> LOCATION: (23)..(24)
<223> OTHER INFORMATION: n is a, c, g, or u

<400> SEQUENCE: 21
```
uuvhbggcua cagugagaug ugnn                                              24

<210> SEQ ID NO 22
<211> LENGTH: 24
<212> TYPE: RNA
<213> ORGANISM: Artificial Sequence
<220> FEATURE:
<223> OTHER INFORMATION: Scrambled passenger strand of miR-1304-5p
<220> FEATURE:
<221> NAME/KEY: misc_feature
<222> LOCATION: (23)..(24)
<223> OTHER INFORMATION: n is a, c, g, or u

<400> SEQUENCE: 22
cacgucucac uguagccvdb gann                                              24

<210> SEQ ID NO 23
<211> LENGTH: 20
<212> TYPE: RNA
<213> ORGANISM: Artificial Sequence
<220> FEATURE:
<223> OTHER INFORMATION: Synthetic mature strand of a negative control
<220> FEATURE:
<221> NAME/KEY: misc_feature
<222> LOCATION: (19)..(20)
<223> OTHER INFORMATION: n is a, c, g, or u

<400> SEQUENCE: 23
guuccaccgu ccucuguann                                                   20

<210> SEQ ID NO 24
<211> LENGTH: 20
<212> TYPE: RNA
<213> ORGANISM: Artificial Sequence
<220> FEATURE:
<223> OTHER INFORMATION: Synthetic passanger strand of the negative
      control
<220> FEATURE:
<221> NAME/KEY: misc_feature
<222> LOCATION: (19)..(20)
<223> OTHER INFORMATION: n is a, c, g, or u

<400> SEQUENCE: 24
uacaggggac gguggaccnn                                                   20

<210> SEQ ID NO 25
<211> LENGTH: 18
<212> TYPE: RNA
<213> ORGANISM: Artificial Sequence
<220> FEATURE:
<223> OTHER INFORMATION: Mature strand of therapeutic agent based on
      miR-1207-3p

<400> SEQUENCE: 25
ucagcuggcc cucauuuc                                                     18

<210> SEQ ID NO 26
<211> LENGTH: 18
<212> TYPE: RNA
<213> ORGANISM: Artificial Sequence
<220> FEATURE:
<223> OTHER INFORMATION: Synthetic passenger strand of therapeutic agent
      based on miR-1207-3p

<400> SEQUENCE: 26
gaaaucaggg ccagcuua                                                     18

<210> SEQ ID NO 27

```
<211> LENGTH: 22
<212> TYPE: RNA
<213> ORGANISM: Artificial Sequence
<220> FEATURE:
<223> OTHER INFORMATION: Synthetic mature strand of therapeutic agent
      based on miR-198

<400> SEQUENCE: 27
gguccagagg ggagauaggu uc                                                  22

<210> SEQ ID NO 28
<211> LENGTH: 22
<212> TYPE: RNA
<213> ORGANISM: Artificial Sequence
<220> FEATURE:
<223> OTHER INFORMATION: Synthetic passenger strand of therapeutic agent
      based on miR-198

<400> SEQUENCE: 28
gaaccuaucu caccucugga uc                                                  22

<210> SEQ ID NO 29
<211> LENGTH: 22
<212> TYPE: RNA
<213> ORGANISM: Artificial Sequence
<220> FEATURE:
<223> OTHER INFORMATION: Synthetic mature strand of therapeutic agent
      based on miR-24-3p

<400> SEQUENCE: 29
uggcucaguu cagcaggaac ag                                                  22

<210> SEQ ID NO 30
<211> LENGTH: 22
<212> TYPE: RNA
<213> ORGANISM: Artificial Sequence
<220> FEATURE:
<223> OTHER INFORMATION: Synthetic passenger strand of therapeutic
      agent based on miR-24-3p

<400> SEQUENCE: 30
cugcuccugc ugaacugagc ua                                                  22

<210> SEQ ID NO 31
<211> LENGTH: 20
<212> TYPE: RNA
<213> ORGANISM: Artificial Sequence
<220> FEATURE:
<223> OTHER INFORMATION: Synthetic mature strand of therapeutic agent
      based on miR-1205

<400> SEQUENCE: 31
ucugcagggu uugcuuugag                                                     20

<210> SEQ ID NO 32
<211> LENGTH: 20
<212> TYPE: RNA
<213> ORGANISM: Artificial Sequence
<220> FEATURE:
<223> OTHER INFORMATION: Synthetic passenger strand of therapeutic agent
      based on miR-1205

<400> SEQUENCE: 32
cucagagcaa acccugcaaa                                                     20

<210> SEQ ID NO 33
<211> LENGTH: 22
```

```
<212> TYPE: RNA
<213> ORGANISM: Artificial Sequence
<220> FEATURE:
<223> OTHER INFORMATION: Synthetic mature strand of therapeutic agent
      based on miR-1304-5p

<400> SEQUENCE: 33
uuugaggcua cagugagaug ug                                          22

<210> SEQ ID NO 34
<211> LENGTH: 22
<212> TYPE: RNA
<213> ORGANISM: Artificial Sequence
<220> FEATURE:
<223> OTHER INFORMATION: Synthetic passenger strand of therapeutic
      agent based on miR-1304-5p

<400> SEQUENCE: 34
cacgucucac uguagccuca ga                                          22

<210> SEQ ID NO 35
<211> LENGTH: 18
<212> TYPE: RNA
<213> ORGANISM: Artificial Sequence
<220> FEATURE:
<223> OTHER INFORMATION: Recognition site that is the antisense
      sequence of miR-1207-3p

<400> SEQUENCE: 35
gaaaugaggg ccagcuga                                               18
```